(12) United States Patent
Sieczkowski et al.

(10) Patent No.: US 10,660,622 B2
(45) Date of Patent: May 26, 2020

(54) PROSTATE BIOPSY NEEDLE

(71) Applicant: DEBN SP. Z O.O., Gdansk (PL)

(72) Inventors: Marcin Sieczkowski, Gdansk (PL);
Artur Gibas, Gdynia (PL); Marcin Matuszewski, Gdansk (PL)

(73) Assignee: DEBN SP. Z O.O., Gdansk (PL)

(*) Notice: Subject to any disclaimer, the term of this patent is extended or adjusted under 35 U.S.C. 154(b) by 184 days.

(21) Appl. No.: 15/545,279

(22) PCT Filed: Jan. 21, 2016

(86) PCT No.: PCT/PL2016/000006
§ 371 (c)(1),
(2) Date: Jul. 20, 2017

(87) PCT Pub. No.: WO2016/118026
PCT Pub. Date: Jul. 28, 2016

(65) Prior Publication Data
US 2018/0168558 A1    Jun. 21, 2018

(30) Foreign Application Priority Data
Jan. 22, 2015 (PL) .......................... 411023

(51) Int. Cl.
*A61B 10/02* (2006.01)
*A61L 31/10* (2006.01)
(Continued)

(52) U.S. Cl.
CPC ...... *A61B 10/0241* (2013.01); *A61B 10/0275* (2013.01); *A61L 31/10* (2013.01);
(Continued)

(58) Field of Classification Search
CPC ............ A61B 10/0241; A61B 10/0275; A61B 5/0266; A61B 2010/0258;
(Continued)

(56) References Cited

U.S. PATENT DOCUMENTS 3,598,127 A * 8/1971 Wepsic ............... A61L 29/16
604/265
3,699,956 A * 10/1972 Kitrilakis ............ A61L 29/16
604/175
(Continued)

FOREIGN PATENT DOCUMENTS

CA      2 586 927 A1    5/2006
JP      2012-11210 A    1/2012
(Continued)

OTHER PUBLICATIONS

N. Mottet et al., "Guidelines on Prostate Cancer" Apr. 2014, 172 pages.
(Continued)

*Primary Examiner* — Navin Natnithithadha
(74) *Attorney, Agent, or Firm* — Masuvalley & Partners

(57) ABSTRACT

Present invention solved the problem of complications occurred during transrectal prostate biopsy, mostly infectious and bleeding complications. Thus, the prostate biopsy needle according to the invention comprising a cannula (1), a pointed stylet (2), which is mounted slidably in the cannula (1), handles (3a, 3b) for the biopsy gun, which are located on the back side of the needle. An inner surface (4) of the cannula (1) and/or an outer surface (5) of the cannula (1) and/or a surface of the stylet (2) is coated with at least one active layer (6) comprising a biologically active agent, wherein the active layer (6) preferably forms a biodegradable structure enabling controlled release of the biologically active agent.

10 Claims, 15 Drawing Sheets

Figure 1:
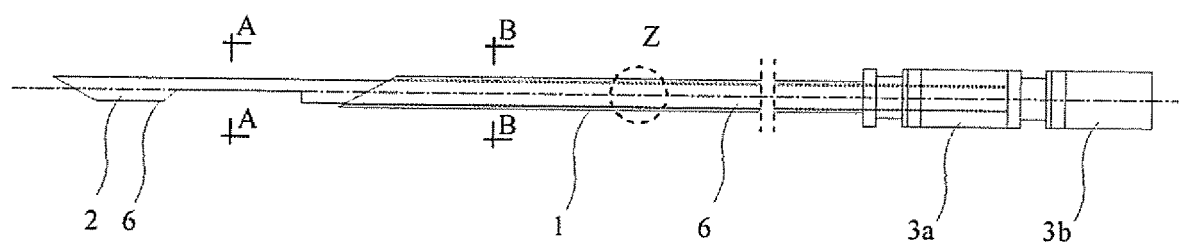

(51) Int. Cl.
*A61L 31/14* (2006.01)
*A61L 31/16* (2006.01)

(52) U.S. Cl.
CPC ............ *A61L 31/146* (2013.01); *A61L 31/148* (2013.01); *A61L 31/16* (2013.01); *A61L 2300/404* (2013.01); *A61L 2300/406* (2013.01)

(58) Field of Classification Search
CPC . A61B 2010/0208; A61B 10/02; A61L 31/10; A61L 31/146; A61L 31/148; A61L 31/16; A61L 2300/404; A61L 2300/406; A61L 31/08
USPC .................................. 600/567, 564, 566, 562
See application file for complete search history.

(56) References Cited

U.S. PATENT DOCUMENTS

| | | | |
|---|---|---|---|
| 4,838,280 A | 6/1989 | Haaga | |
| 5,014,717 A | 5/1991 | Lohrmann | |
| 5,447,724 A | 9/1995 | Helmus et al. | |
| 5,962,620 A * | 10/1999 | Reich .................. | A61K 8/87 528/28 |
| 7,175,611 B2 * | 2/2007 | Mitchnick .............. | A61L 31/16 427/2.12 |
| RE42,982 E * | 11/2011 | Mitchnick .............. | A61L 31/16 424/422 |
| 2003/0236513 A1 | 12/2003 | Schwarz et al. | |
| 2004/0022864 A1 | 2/2004 | Freyman et al. | |
| 2004/0106912 A1 * | 6/2004 | Rosinskaya .......... | A61L 29/085 604/500 |
| 2006/0052757 A1 * | 3/2006 | Fischer, Jr. .............. | A61F 2/82 604/265 |
| 2010/0130850 A1 | 5/2010 | Pakter | |
| 2011/0015724 A1 * | 1/2011 | Kocher ................. | A61L 29/085 623/1.42 |
| 2011/0022005 A1 * | 1/2011 | Kocher ................... | A61L 31/10 604/264 |
| 2012/0059247 A1 | 3/2012 | Speeg et al. | |
| 2013/0324910 A1 | 12/2013 | Ohri et al. | |
| 2014/0014336 A1 | 1/2014 | Q | |

FOREIGN PATENT DOCUMENTS

| | | |
|---|---|---|
| JP | 2012-527986 A | 11/2012 |
| PL | 214742 B1 | 9/2013 |
| WO | 00/10622 A1 | 3/2000 |
| WO | 2010/138944 A2 | 12/2010 |
| WO | 2012/132774 A1 | 10/2012 |
| WO | WO 2014/014336 A1 | 1/2014 |
| WO | 2014/064304 A1 | 5/2014 |

OTHER PUBLICATIONS

N. Blanchemain et al., "Vascular PET Prostheses Surface Modification with Cyclodextrin Coating: Development of a New Drug Delivery System", Elsevier Ltd., Eur J Vasc Endovasc Surg 29, 2005, p. 628-632, http://www.sciencedirect.com.

Joseph B. Ciolino et al., "A Drug-Eluting Contact Lens", Investigative Ophthalmology & Visual Science, Association for Research in Vision and Ophthalmology, Jul. 2009, Vo. 50, No. 7, p. 3346-3352.

Carolina D'Elia et al., "Upgrading and upstaging in prostate cancer: From prostate biopsy to radical prostatectomy", Department of surgery, Urology Clinic, A.O.U.I. Verona, Italy, Jun. 17, 2014, Molecular and Clinical Oncology 2: p. 1145-1149.

Michael A. Liss et al., "Prevalence and Significance of Fluoroquinolone Resistant *Escherichia coli* in Patients Undergoing Transrectal Ultrasound Guided Prostate Needle Biopsy", Apr. 2011 by American Urological Association Education and Research, Inc., 185(4) p. 1283-1288.

Jae Hyung Park et al., "Norfloxacin-releasing urethral catheter for long-term catheterization", J. Biomater. Sci. Polymer Edn, vol. 14, No. 9, p. 951-962 (2003), www.vsppub.com.

Sandeep K. Mishra et al., "Mechanically stable antimicrobial chitosan-PVA-silvernanocomposite coatings deposited on titanium implants", Carbohydrate Plymers 121 (2015) p. 37-48, Elsevier: www.elsevier.com/locate/carbpol.

WIPO, International Preliminary Examining Authority (European Patent Office), International Preliminary Report on Patentability dated Apr. 26, 2017 in International Patent Application No. PCT/PL2016/000006, 7 pages.

WIPO, European International Search Authority, International Search Report and Written Opinion dated Jul. 26, 2016 in International Patent Application No. PCT/PL2016/000006, 14 pages.

Marcin Sieczkowski et al., "Drug-Eluting Biopsy Needle as a Novel Strategy for Antimicrobial Prophylaxis in Transrectal Prostate Biopsy", Technology in Cancer Research & Treatment, 2017, vol. 16(6) 1038-1043.

JPO, Notice of Reasons for Refusal dated Nov. 5, 2019 in Japanese Patent Application No. 2017-557265, total 7 pages with English translation.

* cited by examiner

PROSTATE BIOPSY NEEDLE

RELATED APPLICATIONS

This application is the U.S. National Phase of and claims priority to International Patent Application No. PCT/PL2016/000006, International Filing Date Jan. 21, 2016, entitled Prostate Biopsy Needle; which claims benefit of Polish Application No. PL P.411023 filed Jan. 22, 2015; both of which are incorporated herein by reference in their entireties.

The present invention relates to the prostate biopsy needle for performing transrectal prostate biopsy.

Prostate cancer is the most common malignancy diagnosed in men in Europe, Australia and North America. The average chance to develop this cancer during lifetime is approximately 15% and its incidence rate is estimated to be about 150 per 100 000 male. It is associated with high costs of diagnosis and treatment, which are estimated at 8.43 billion € per year in Europe.

Transrectal ultrasound-guided prostate biopsy is the standard method for pathological diagnosis of prostate cancer and is one of the most common urological procedures performed around the world. Only in the United States of America, there are approximately 800 000 prostate biopsies performed annually.

Patent application U.S. Pat. No. 5,014,717 discloses a punch-biopsy apparatus for prostate biopsy comprising a cannula, a stylet that is mounted slidably in the cannula, handles for a biopsy gun which are located on the back side of the needle. Known prostate biopsy needle is inserted into the prostate under transrectal ultrasound guidance. Triggering the spring mechanism results in a rapid sliding of the stylet, and then pulling the cutting cannula on the stylet. This enables to collect the tissue sample from the desired area of a prostate. During the biopsy at least eight cores should be taken from different parts of the prostate. This multiplies the risk of complications mentioned below.

The most common complications following transrectal prostate biopsy performed by known prostate biopsy needles are hematuria and hematospermia. However, the most serious clinical problems are infectious complications occur after the prostate biopsy. During the procedure, after introduction of the needle through the rectum, the intestinal bacteria are transferred into the blood and the prostate. Patients undergoing prostate biopsy are exposed to urinary tract infections, prostatitis, and even severe septic complications. Therefore, it is recommended that periprocedural oral antibacterial prophylaxis should be administrated. The most commonly used antibiotics in antibacterial prophylaxis prior transrectal prostate biopsy are oral fluoroquinolones. In recent years, numerous scientific publications have reported the rapid spread of intestinal bacterial strains resistant to this group of antibiotics. This phenomenon is responsible for an increase in the percentage of severe infectious complications occurring after the prostate biopsy performed by the known biopsy prostate needle.

Hitherto, an effective and fully accepted strategy to reduce the infections caused by transrectal prostate biopsy still has not been defined. Attempts to use oral or intravenous antibiotics from other groups appear to be insufficiently effective. While, simultaneous use of multiple antibiotics in prophylaxis can result in significant side effects.

The known prostate biopsy needle does not allow to overcome the problem of hematuria, hematospermia and infectious complications which occur as a result of transrectal invasive procedures of prostate biopsy.

A known solution of this problem is a transperineal prostate biopsy. However this method has some significant disadvantages including the need for epidural or general analgesia, which is an additional burden for the patient and special equipment requirements, which increases the costs of diagnosis.

There are known multiple methods to modify the surface of medical devices for insertion into human organs and body cavities for long-term period. Examples of such medical devices include: stents, vascular grafts, catheters, urological, orthopedic implants and contact lenses. Their surface is usually coated with a bioactive layer. The presence of a bioactive layer enables to release biologically active substances from the surface of such devices. Biologically active agents are usually used to reduce the risk of vessels occlusion (stents and vascular grafts) or prevent infection (orthopedic implants or dental catheters, urology, contact lenses, vascular prostheses) that can develop due to long exposure to medical device implanted into the body.

There are also known urological catheters, contact lenses, vascular, orthopedic or dental implants, which surface is coated with a bioactive layer releasing antimicrobial agents. Furthermore, there are known medical devices such as catheters, urological and vascular stents, which surface is coated with an additional protective layer that enables stable release of active agents and/or with additional binder layer which strengthens the connection of bioactive layer with the surface of the medical device.

The application of beta-cyclodextrin complex with vancomycin on the surface of the vascular prosthesis made of poly(ethylene terephthalate) is known from the publication [Blanchemain N et al. European Journal of Vascular and Endovascular Surgery 2005, 29, 628-632]. Cyclodextrins are cyclic oligosaccharides with a toroid-shaped molecular structure, characterized by a hydrophilic outer surface and a lipophilic central cavity which enable them to form inclusion compounds with antibiotics.

The formation of the antimicrobial bioactive layer on the surface of titanium medical implant using poly(vinyl alcohol), chitosan and silver ions is known from the publication [Mishra S K et al. Mechanically stable antimicrobial chitosan-PVA-silver nanocomposite coatings Deposited on Titanium Implants, Carbohydrate Polymers, 2015, 121, 37-48]. The contact lenses with a bioactive layer formed of poly(L-glutamic acid) containing ciprofloxacin are known from literature [Ciolino J B et al., Drug-Eluting A Contact Lens. Investigative Ophthalmology and Visual Science, 2009, 50 (7), 3346-3352].

Patent No PL214742 discloses a method for preparing an antibacterial layer on the surface of the catheters by immobilization of antimicrobial substances due to fixed connection through the use of the polysaccharide.

There are known silicone catheters with antibacterial properties, where the bioactive layer is formed by immersing the catheter in a solution composed of polymers: poly (ethylene-co-vinyl acetate), poly(ethyleneoxide) and poly (dimethylsiloxane) containing antibiotics [Park J H et al., Journal of Biomaterials Science, Polymer Edition, 2003, 14 (9), 951-962].

All of the known medical devices coated with bioactive layer are designed for implantation into the human body permanently or for a long period of time. The biopsy prostate needle is not such a device since it is introduced into the body for relatively short time only during duration of procedure.

The object of the invention is to provide the prostate biopsy needle, which reduces the periprocedural complications. The invention therefore relates to prostate biopsy needle, which provide protection against potential infection and perioperative bleeding complications. In particular the biopsy needle with specific construction that allow the administration of biologically active agents during the prostate biopsy.

Unexpectedly, we found that adequate and very distinctive coating of biopsy needle with bioactive layer or relevant mechanical construction of a biopsy needle enables release or direct application of the biological active compounds to a prostate gland.

Thus according to the invention the prostate biopsy needle comprising a cannula, a pointed stylet mounted slidably in the cannula, handles for a biopsy gun located on the back side of the needle, characterized in that an outer surface of the cannula and/or a surface of the stylet is coated with at least one active layer comprising a an antibacterial substance. The active layer preferably forms a biodegradable structure enabling controlled release of the biologically active agent.

In a preferred embodiment, the outer surface of the cannula and/or the surface of the stylet form an extended surface in a form of a grooved and/or rough and/or porous surface.

In a preferred embodiment, the extended surface forms pits with depth ranged from 0.001 mm to 0.1 mm, preferably from 0.01 mm to 0.06 mm.

In a further embodiment, the part of outer surface of the cannula is coated with the active layer, wherein the coated part is an area ranged from 0.1 cm to 10 cm in length, preferably from 4 cm to 8 cm, and/or the part of the surface of the stylet is coated with the active layer, wherein the coated part is the area ranged from 0.1 cm to 10 cm in length, preferably from 4 cm to 8 cm. In an embodiment, the coated part of the outer surface of the cannula extends from a tip of the cannula and/or the coated part of the surface of the stylet extends from the tip of the stylet.

In a further embodiment, the active layer is applied on a binder layer wherein the outer surface of the cannula and/or the surface of stylet is coated with the binder layer.

In a further embodiment, the active layer contains a binder agent.

In a further embodiment, the surface of active layer is coated with a protective layer enabling stable release of the biologically active agent, preferably in the form of polymer layer.

In an embodiment, the protective layer has a form of a fine mesh with the cells size from 1 μm to 500 μm, preferably 10 μm to 100 μm.

In an embodiment, the antibacterial substance is an antibiotic and/or the chemotherapeutic agent and/or zinc ions and/or silver ions.

To solve the problem, the present invention also provide prostate biopsy needle comprising a cannula and pointed stylet mounted slidably in the cannula which is characterized by longitudinal pass-through-hole channel formed in the wall of the cannula. The channel has closed profile in cross-section view, and the channel extends through the entire length of the wall of cannula or the part the length thereof. In preferred embodiment of this invention, the channel is circular-shaped in cross-section with the diameter of 0.1 mm to 2.0 mm, preferably from 0.5 mm to 0.7 mm.

In further embodiment, the channel protrudes over the outer surface of the cannula, preferably protrudes over the area of 130 mm to 155 mm from the cannula.

According to the invention, biopsy needle enables for direct delivery surface elution of different antibiotics, and/or anti-inflammatory drugs and/or other substances with a biological activity into the prostate. This does not require additional punctures of the prostate since biologically active agents are released simultaneously during prostate biopsy. The positive effect of this invention is that biologically active agents are introduced through the needle precisely to the starting point of potential infection. This allows for reduction or complete elimination of oral or intravenous antimicrobial prophylaxis prior transrectal prostate biopsy. Furthermore, the effective dose of drugs administered directly into the prostate may be significantly lower than in intravenous or oral form. The invention enables simultaneous topical application of a set of antibiotics, which can broaden the spectrum of antimicrobial protection, with a lower risk of side effects. The invention set a completely new approach of periprocedural antimicrobial prophylaxis for prostate biopsy. The invention also enables the simultaneous administration of several active agents like anesthetics and/or anti-inflammatory and/or antibacterial and/or anti-hemmorrhagic substances.

The invention is shown in more details in the examples and drawings wherein

Figure 2:
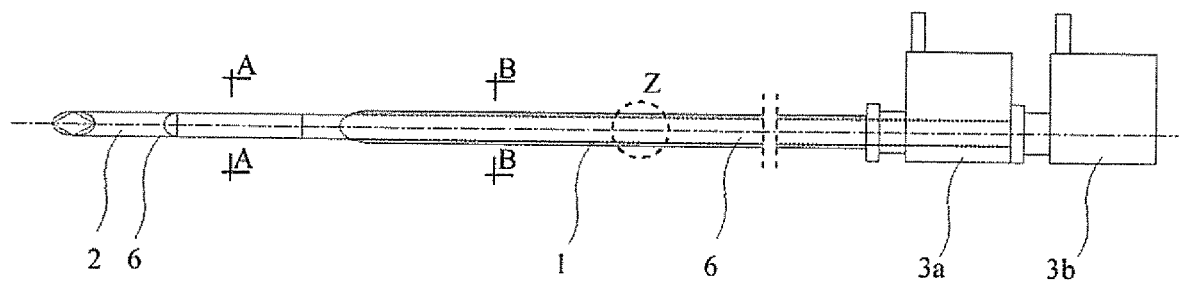
Figure 3:
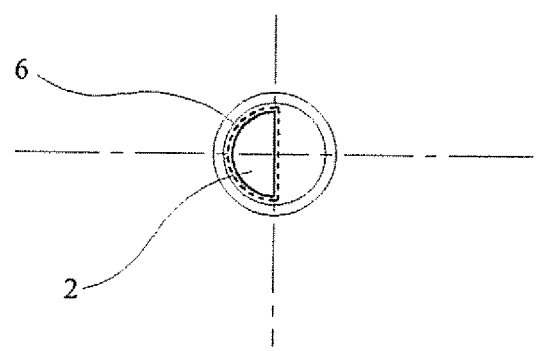
Figure 4:
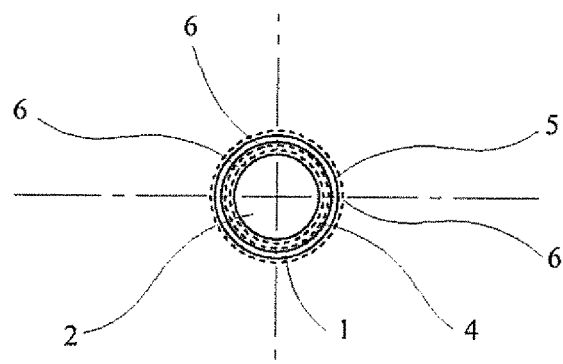
Figure 5:
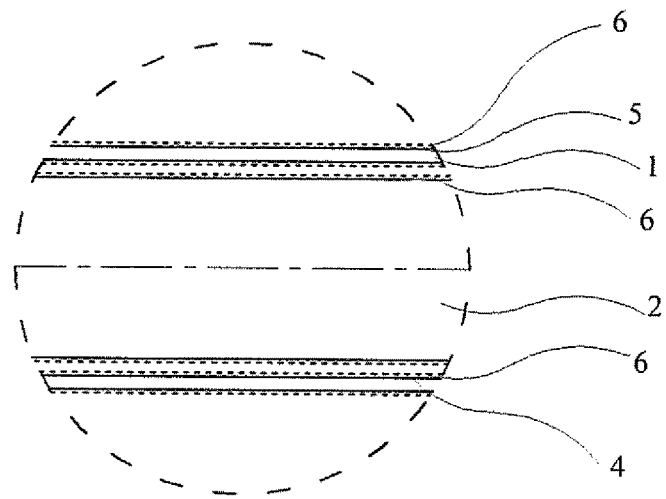
Figure 6:
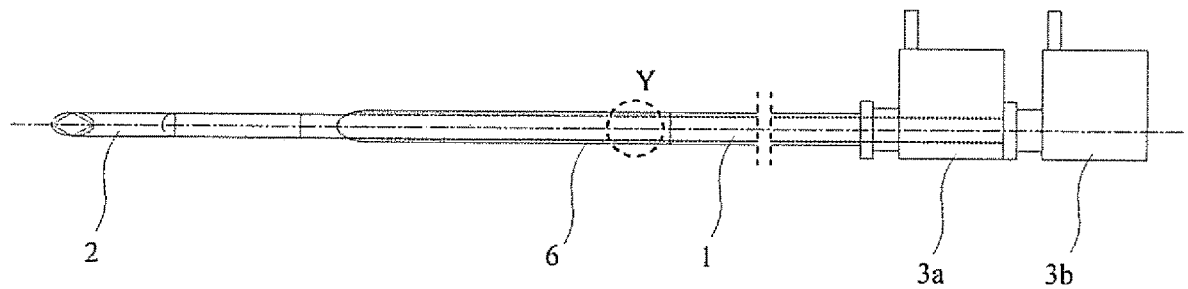
Figure 7:
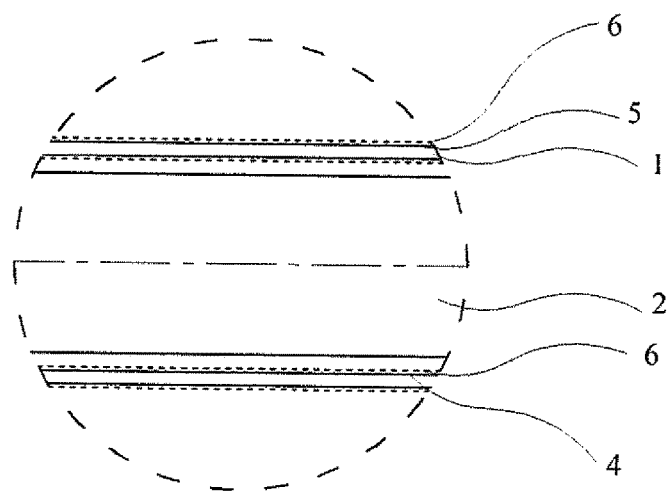
Figure 8:
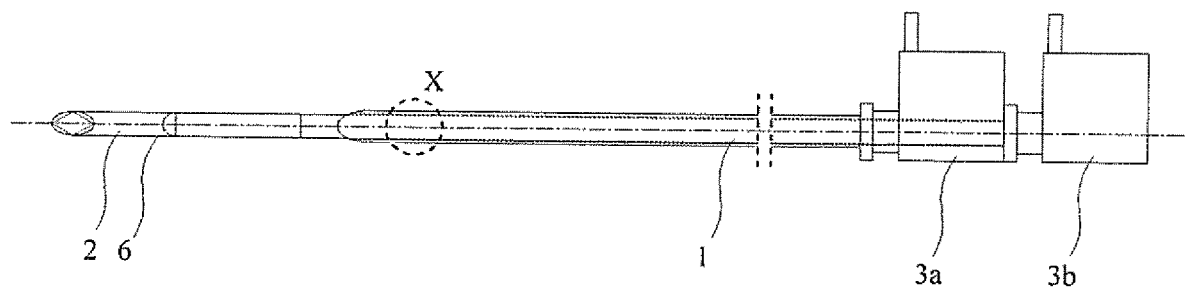
Figure 9:
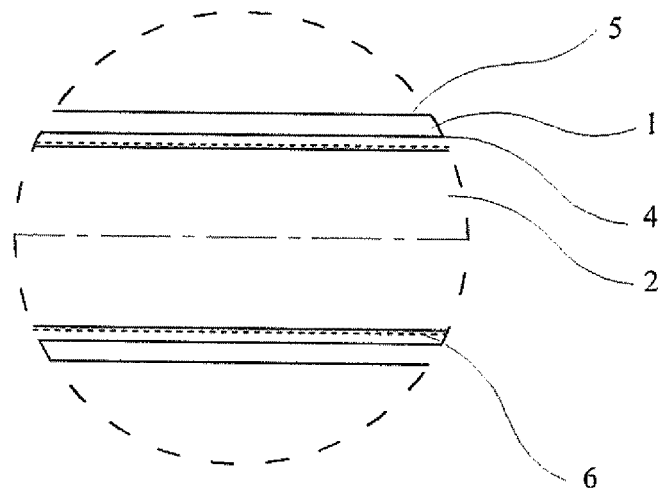
Figure 10:
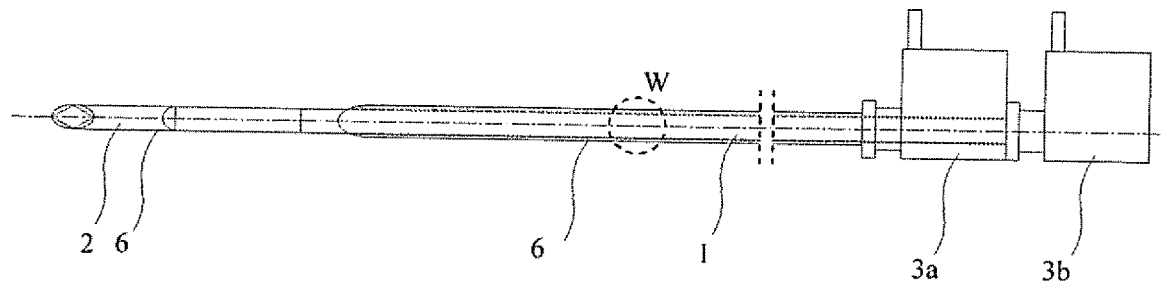
Figure 11:
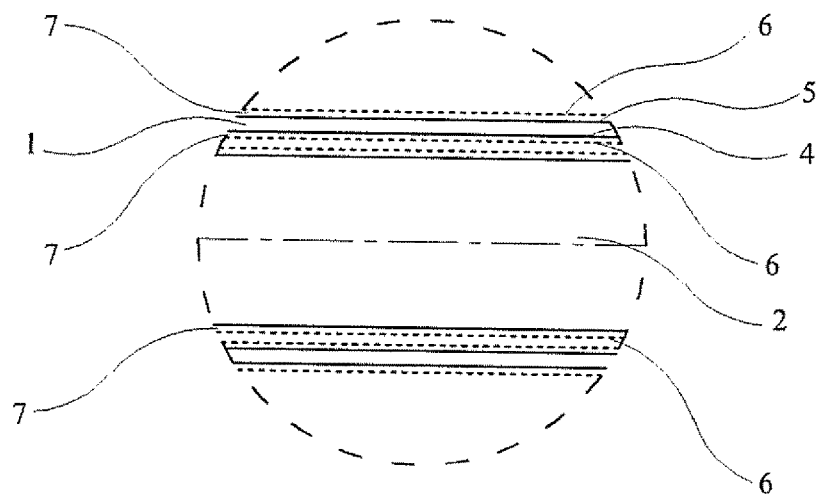
Figure 12:
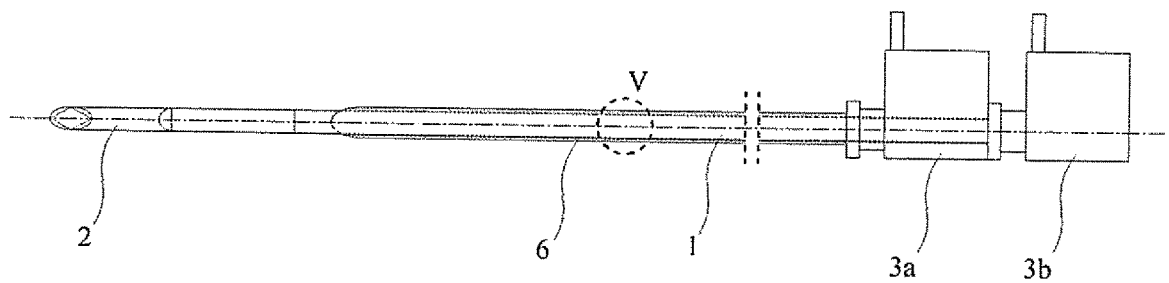
Figure 13:
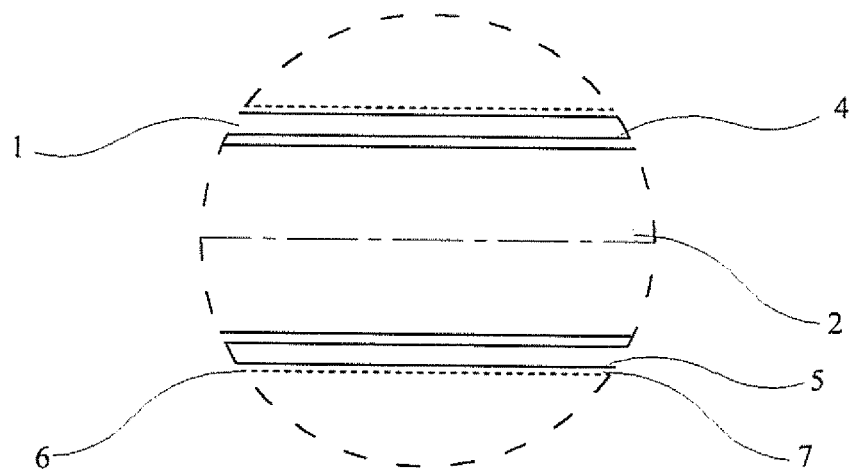
Figure 14:
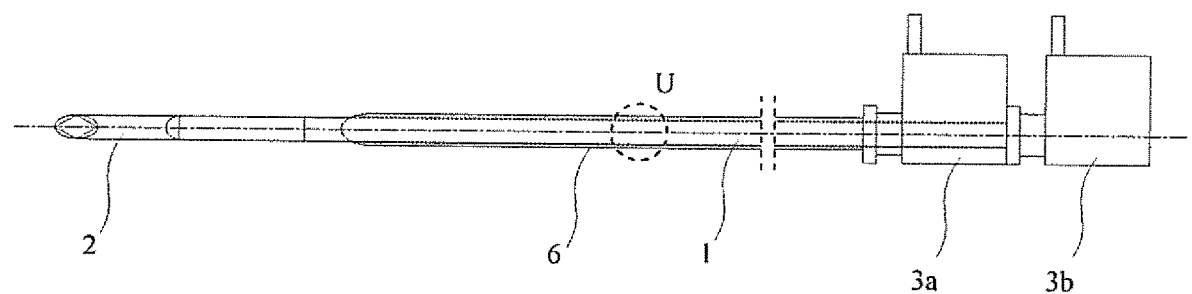
Figure 15:
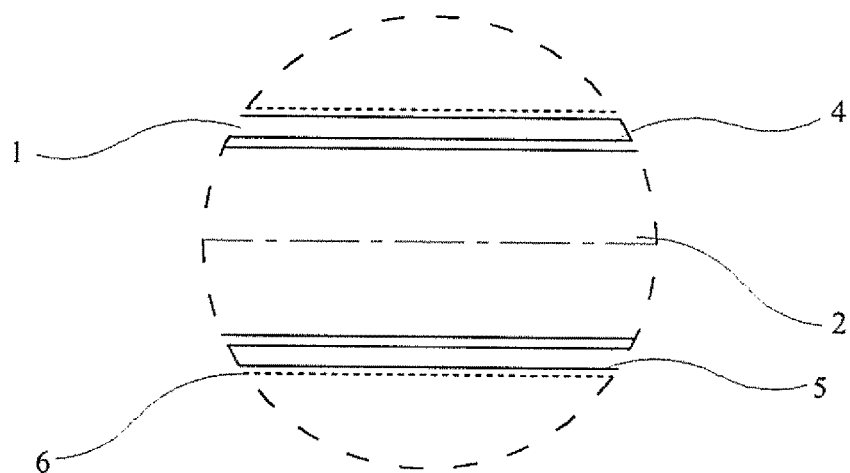
Figure 16:
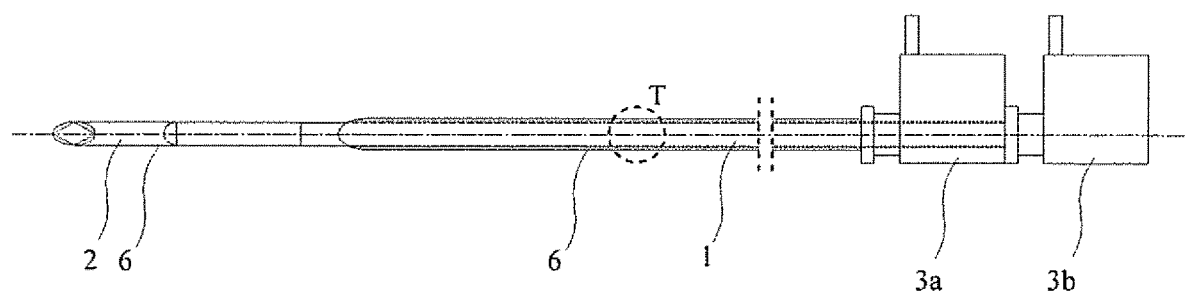
Figure 17:
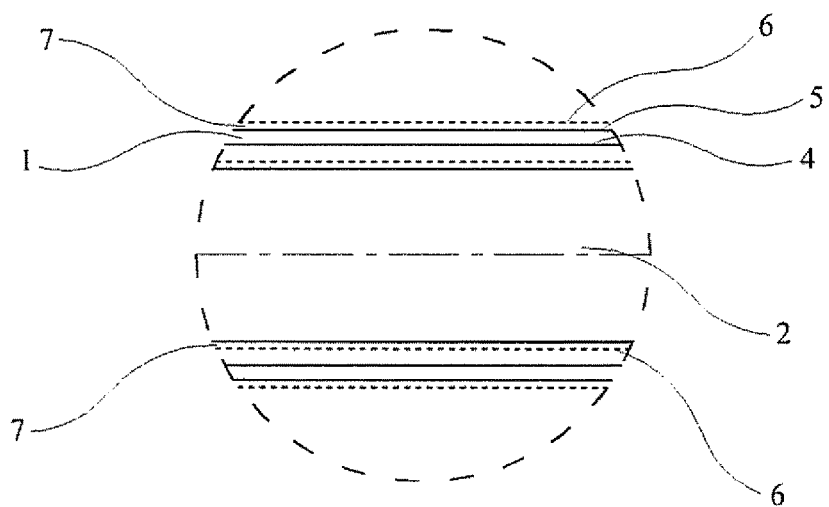
Figure 18:
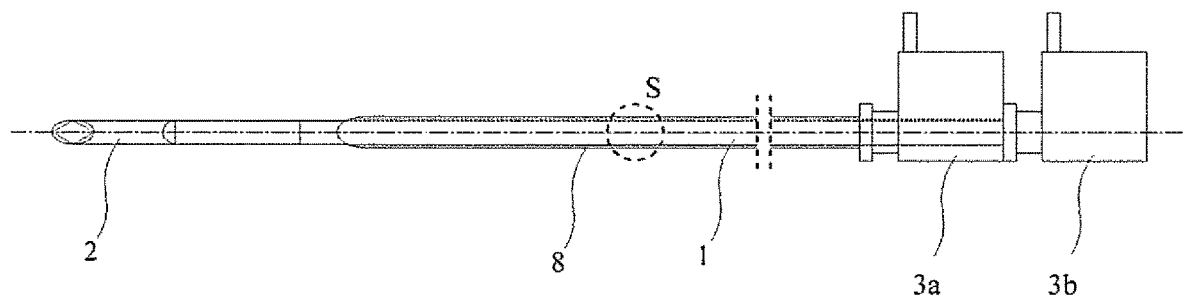
Figure 19:
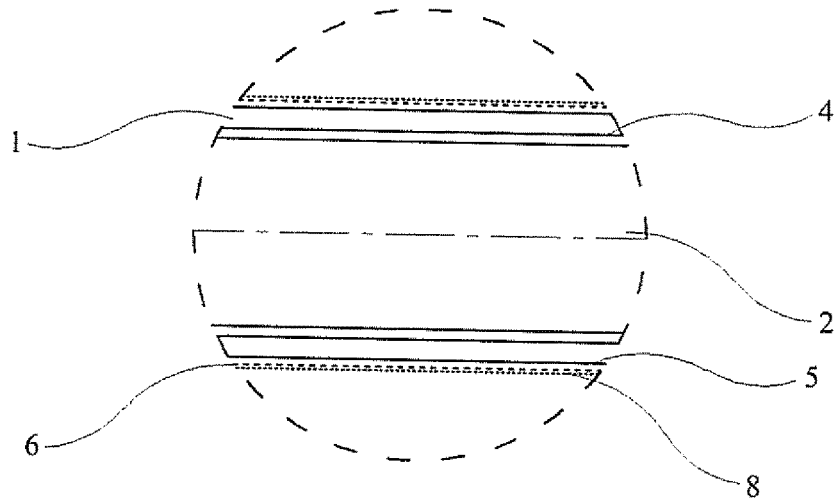
Figure 20:
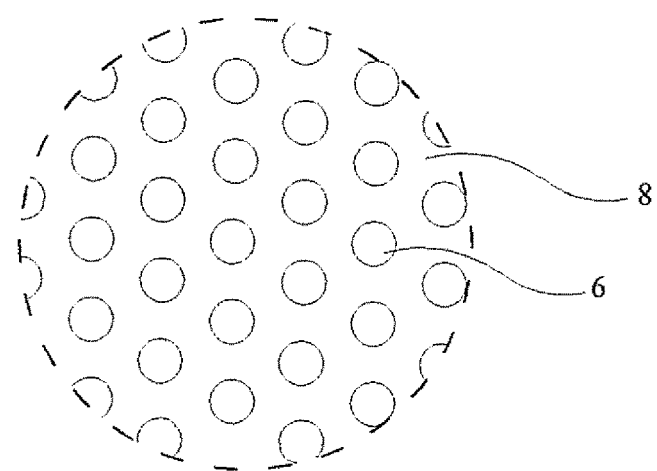
Figure 21:
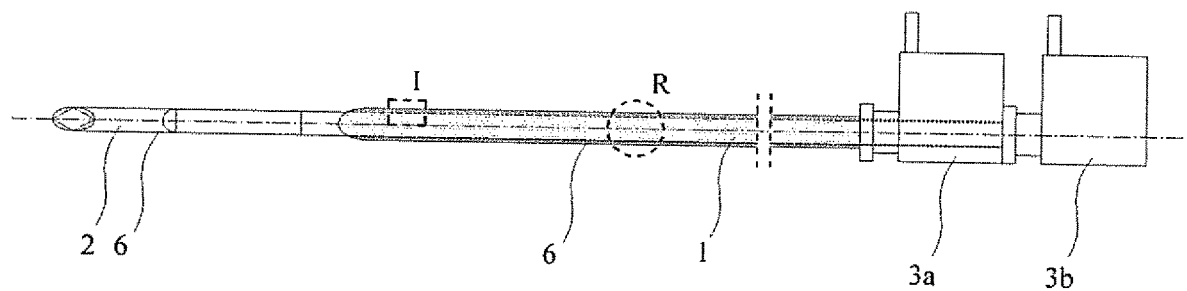
Figure 22:
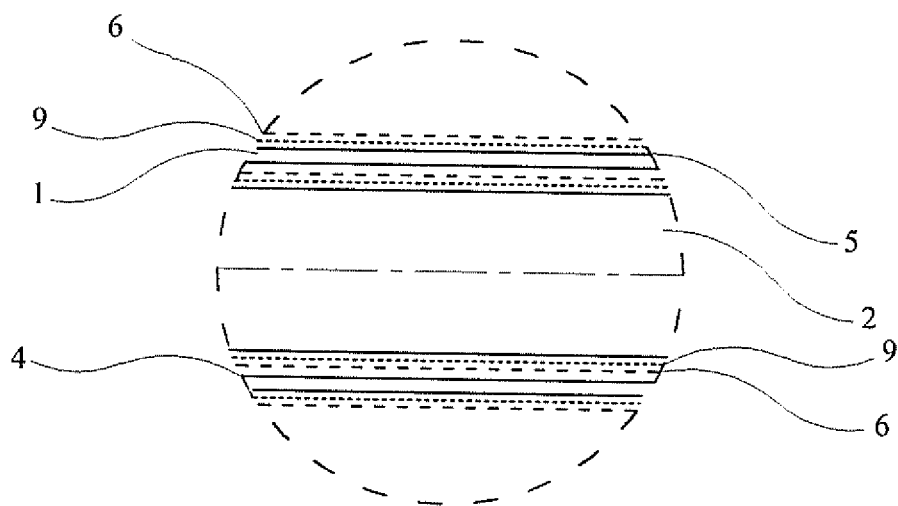
Figure 23:
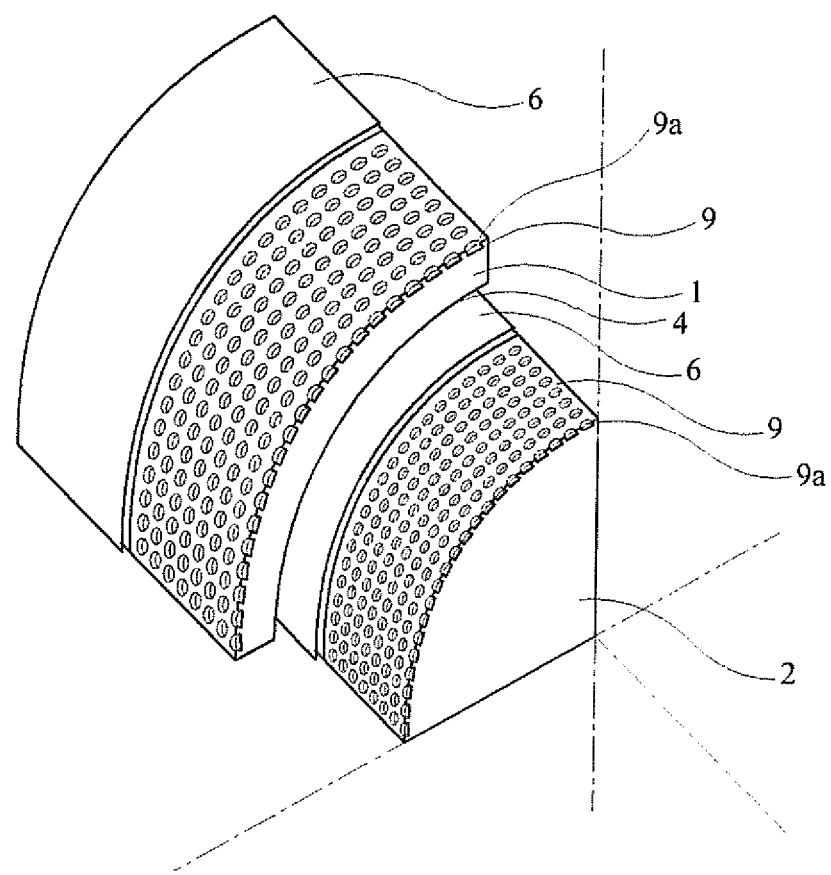
Figure 24:
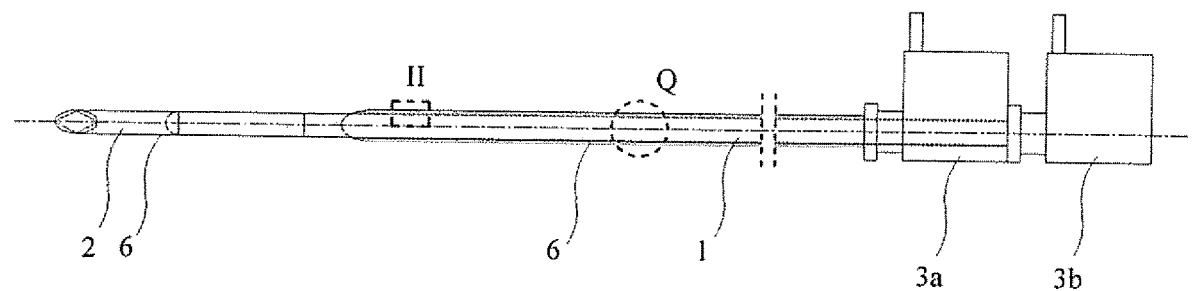
Figure 25:
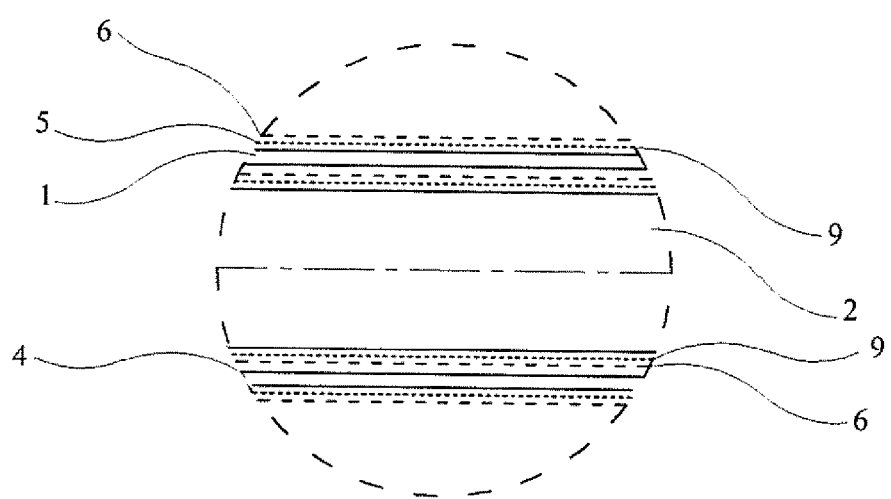
Figure 26:
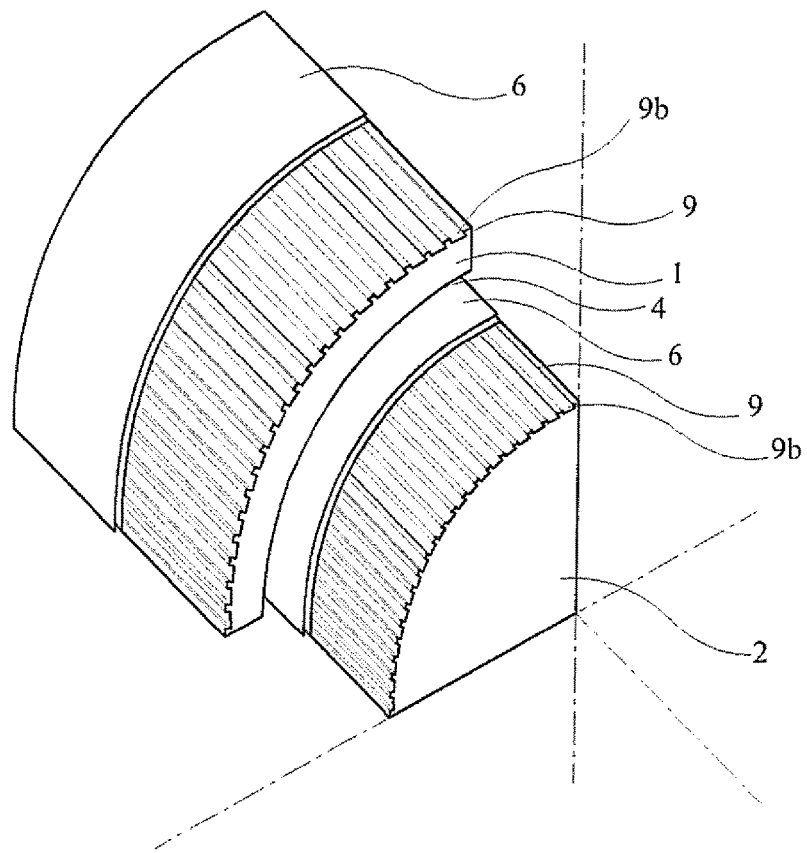
Figure 27:
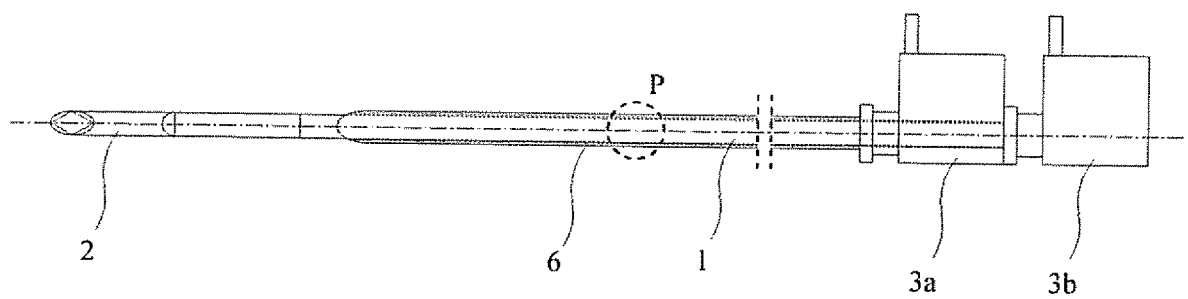
Figure 28:
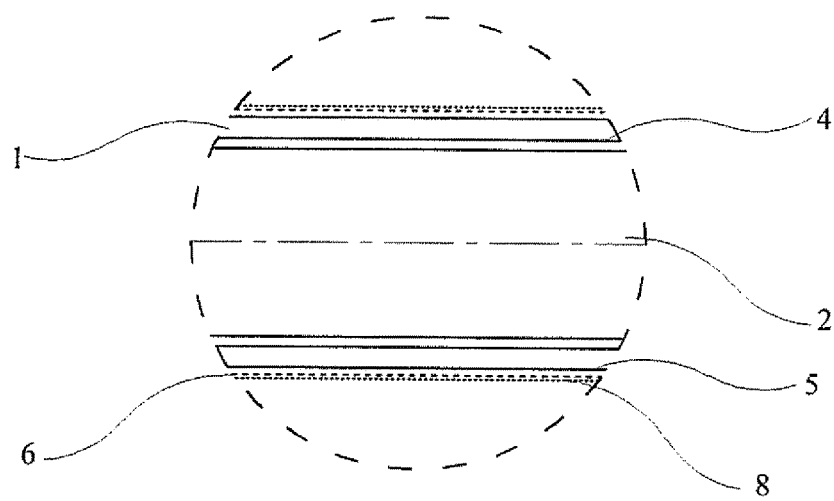
Figure 29:
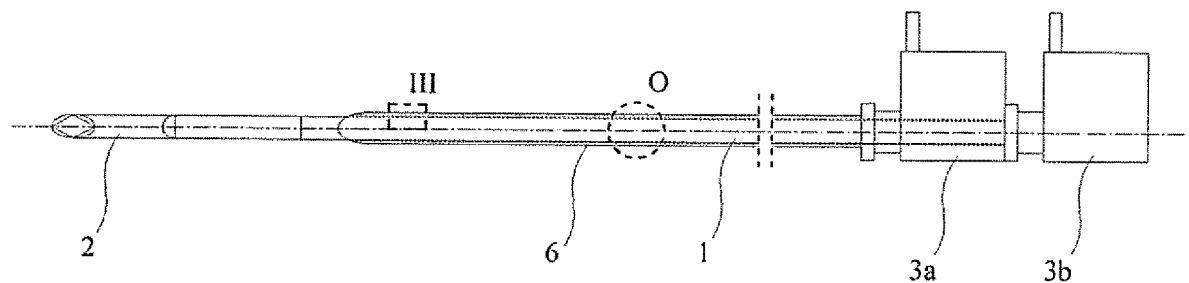

FIG. 1 shows a biopsy needle in a top view,

FIG. 2 biopsy needle in a side view,

FIG. 3 a cross section of the stylet taken along the line A-A in FIG. 1,

FIG. 4 a cross-section through the stylet and cannula along line B-B in FIG. 1,

FIG. 5 enlarged longitudinal section of the stylet and the cannula at the point Z in FIG. 1 and FIG. 2;

FIG. 6 biopsy needle in a side view, in a further embodiment,

FIG. 7 enlarged longitudinal section of the stylet and the cannula at the point Y of FIG. 6;

FIG. 8 biopsy needle in a side view, in a further embodiment,

FIG. 9 enlarged longitudinal section of the stylet and the cannula at the point X of FIG. 8;

FIG. 10 biopsy needle in a side view, in a further embodiment,

FIG. 11 enlarged longitudinal section through the stylet and cannula in place W of FIG. 10;

FIG. 12 biopsy needle in a side view, in a further embodiment,

FIG. 13 enlarged longitudinal section of the stylet and the cannula at the point V of FIG. 13;

FIG. 14 biopsy needle in a side view, in a further embodiment,

FIG. 15 enlarged longitudinal section of the stylet and the cannula at the point U of FIG. 14;

FIG. 16 biopsy needle in a side view, in a further embodiment,

FIG. 17 enlarged longitudinal section of the stylet and the cannula at the point T of FIG. 16;

FIG. 18 biopsy needle in a side view, in a further embodiment,

FIG. 19 englarged longitudinal section of the stylet and the cannula at the point S of FIG. 18, FIG. 20 enlarged cannula surface;

FIG. 21 biopsy needle in a side view, in a further embodiment,

FIG. 22 enlarged longitudinal section of the stylet and the cannula at the point R of FIG. 21, FIG. 23 enlarged axonometric view of the extended layers from segment I of the biopsy needle from FIG. 21;

FIG. 24 biopsy needle in a side view, in a further embodiment,

FIG. 25 enlarged longitudinal section of the stylet and the cannula at the point Q of FIG. 24, FIG. 26 enlarged axonometric view of the extended layers from segment II of the biopsy needle from FIG. 24;

FIG. 27 biopsy needle in a side view, in a further embodiment,

FIG. 28 enlarged longitudinal section of the stylet and the cannula at the point P of FIG. 27;

FIG. 29 biopsy needle in a side view, in a further embodiment, in

Figure 30:
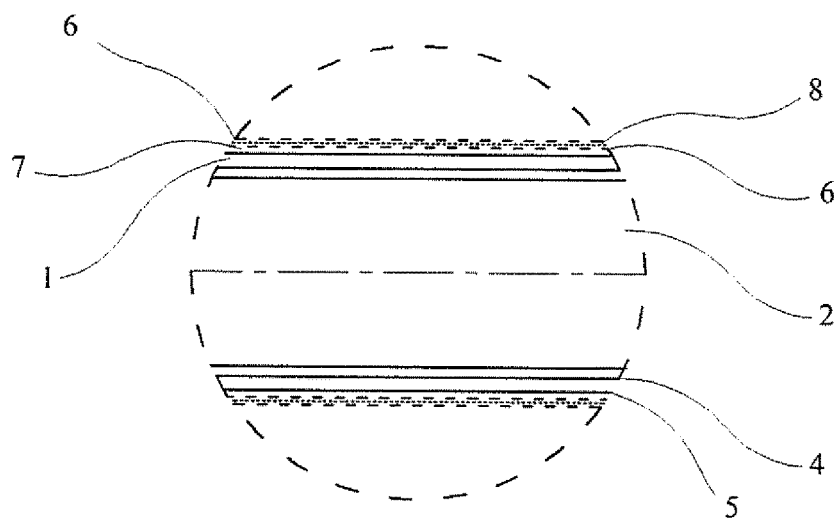
Figure 31:
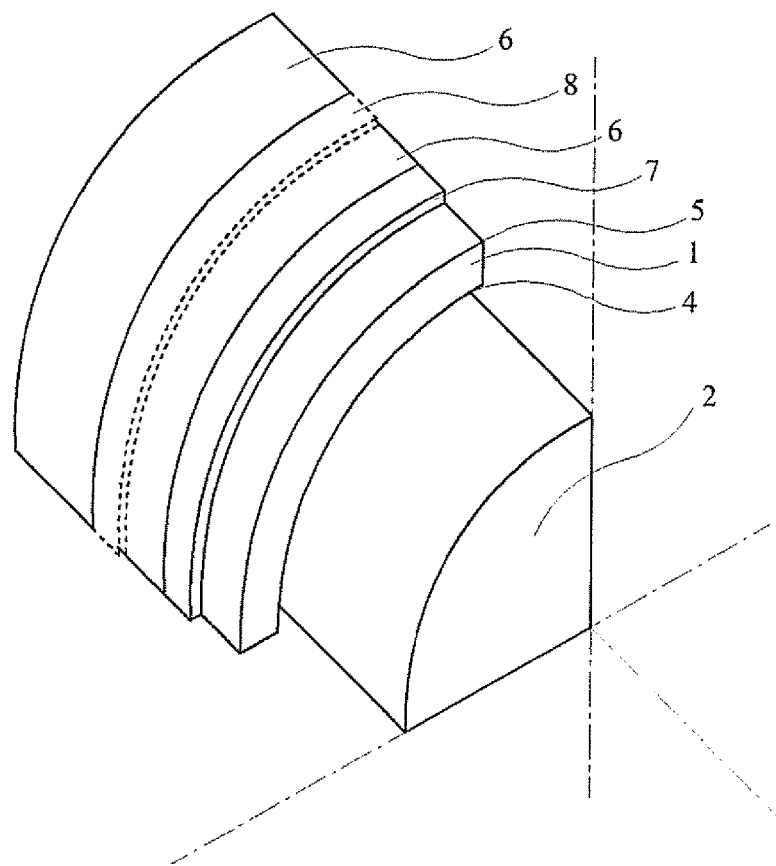
Figure 32:
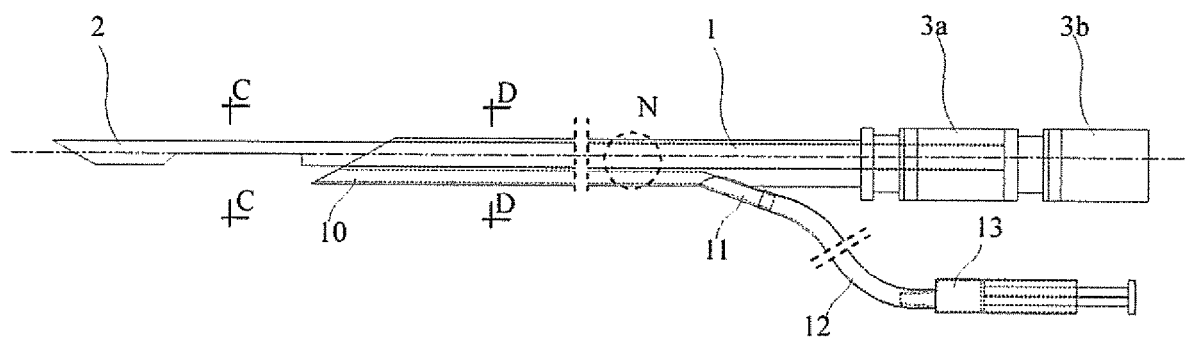
Figure 33:
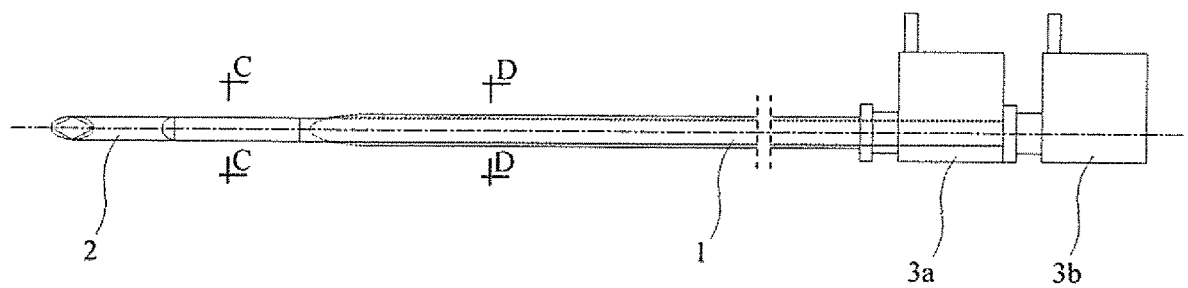
Figure 34:
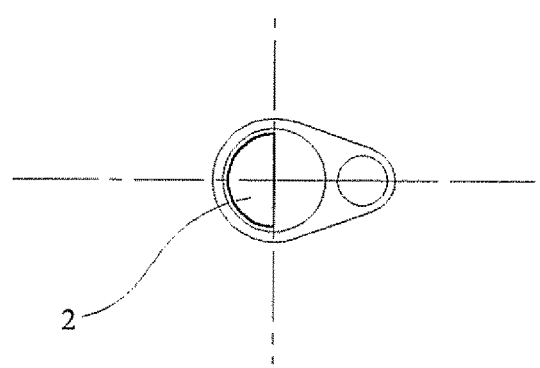
Figure 35:
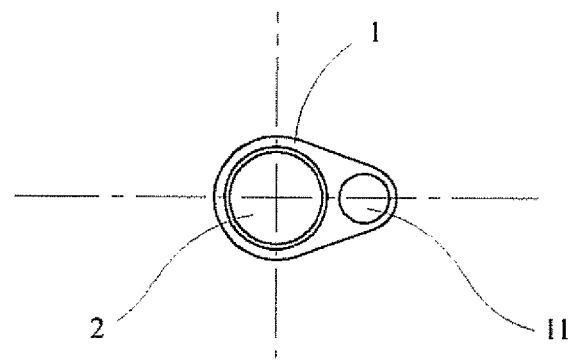
Figure 36:
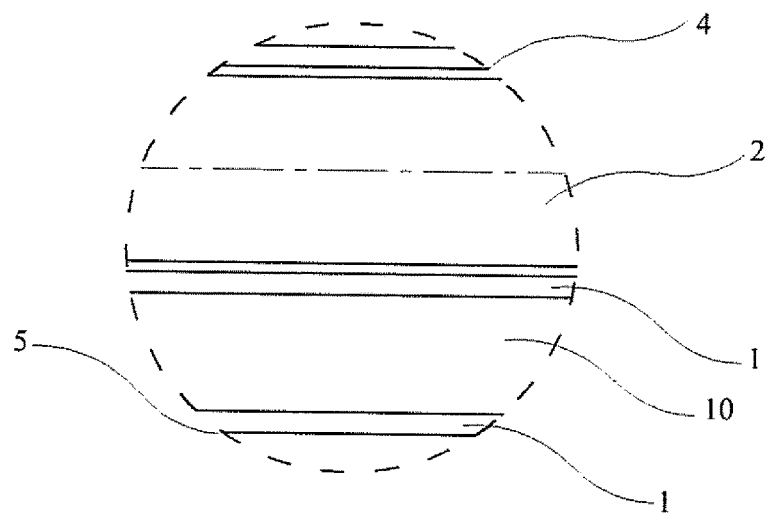
Figure 37:
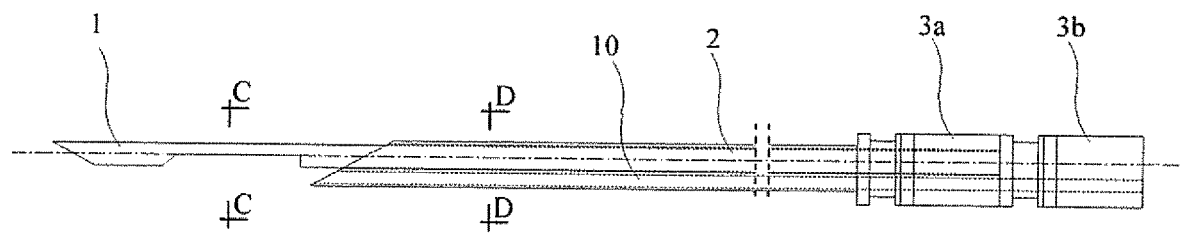
Figure 38:
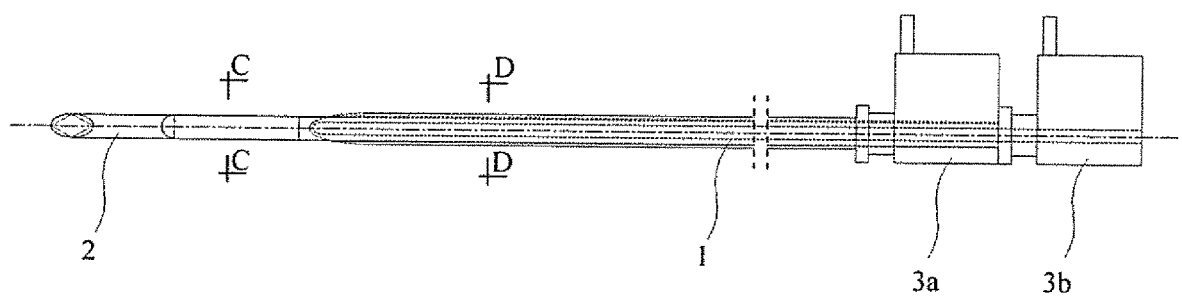
Figure 39:
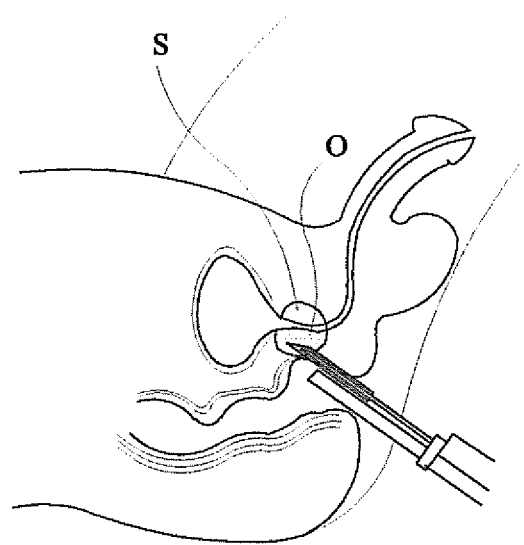

FIG. 30 enlarged longitudinal section of the stylet and the cannula at the point O from FIG. 29, FIG. 31 enlarged axonometric view of the extended layers from segment III of the biopsy needle from FIG. 29;

FIG. 32 biopsy needle in a top view, in a further embodiment,

FIG. 33 biopsy needle in a side view,

FIG. 34 cross-section of the stylet taken along the line CC of FIGS. 32, 33, 37 and 38;

FIG. 35 is a cross section of the stylet and the cannula along the line DD of FIGS. 32, 33, 37 and 38;

FIG. 36 enlarged longitudinal section through the stylet and cannula N of FIG. 32;

FIG. 37 biopsy needle in a top view, in a further embodiment,

FIG. 38 biopsy needle in a side view,

FIG. 39 anatomical chart of prostate surrounding during biopsy.

EXAMPLE 1

A steel biopsy needle with 200 mm length, comprises a pointed cannula 1, pointed stylet 2 mounted slidably in the cannula 1 and in the back the polypropylene holders for the biopsy gun—a cannula holder 3a and stylet holder 3b. The outer diameter of the cannula 1 is 1.93 mm, the inner diameter of the cannula 1 is 1.70 mm, and the stylet 2 diameter is 1.65 mm.

The inner surface 4 of the cannula 1 and the outer surface 5 of the cannula 1 and the surface of the stylet 2, over the entire length of the steel needles are coated with the active layer 6 containing the biologically active agents, as shown in FIGS. 1-5. Active layer 6 has a biodegradable form allows for the controlled release of the biologically active agent by dissolving in water contained in the blood and biopted tissue. The active layer contains two antibiotics—ciprofloxacin and amikacin which form inclusion complex with β-cyclodextrin. An active layer 6 was obtained by mixing in a centrifuge (5 min, 30 rpm), ciprofloxacin, amikacin and β-cyclodextrin in a molal ratio 1:1:2. The mixture of compounds was dissolved in 0.14% aqueous solution of a nitrogen hydride (III). The obtained solution was filtered. After immersion of the steel cannula 1 and stylet 2 in solution, the freeze-drying process was carried out to perform the active layer 6 fixation. As shown in FIG. 39 by using the biopsy gun and a biopsy needle under transrectal ultrasound, prostate cores s were collected in a standard way. During the procedure, ciprofloxacin and amikacin were directly release from the biodegradable active layer 6 into the prostate tissue by disintegration of inclusion complex of β-cyclodextrin with antibiotics. In vitro and in vivo studies confirmed the release of drugs from the active layer 6 applied to the steel surface of the biopsy needle and the antibacterial effect in the action area o of bioactive agents.

EXAMPLE 2

The needle is made as described in Example 1, except that the inner surface 4 of the cannula 1 and part of the outer surface 5 of the cannula 1, 5 cm long from the tip of it, is coated with an active layer 6 as shown in FIG. 6 and FIG. 7. The active layer 6 contains two antibiotics: ciprofloxacin and amikacin, as described in Example 1.

EXAMPLE 3

The needle is made as described in Example 1, except that the part of stylet 2 surface, 7 cm long from the tip of it, is coated with an active layer 6, as shown in FIG. 8 and FIG. 9. The active layer 6 contains two antibiotics: ciprofloxacin and amikacin, as described in Example 1.

EXAMPLE 4

The needle is made as described in Example 1, except that the active layer 6 is applied on the binder layer 7, which is placed on the outer surface 5 of the cannula 1 and the inner surface 4 of the cannula 1 and the surface of the stylet 2, as shown in FIG. 10 and FIG. 11. The binder layer 7 is made of poly(vinyl alcohol). The binder layer 7 was obtained by dipping the cannula 1 in a solution of acetone and drying, and then dipping in an aqueous solution of 0.5 mM/L, of poly(vinyl alcohol) (molecular weight of 49,000 g mol-1). On such binder layer 7 the active layer 6, obtained as described in Example 1, was applied.

EXAMPLE 5

The needle is made as described in Example 1, except that the active layer 6 is applied on the binder layer 7, which covers the outer surface 5 of the cannula 1, as shown in FIG. 12 and FIG. 13. The binder layer 7 is made of polyethylene (vinyl alcohol). Binder layer 7 was obtained as described in Example 4 except that in the solution was immersed temporarily sealed cannula 1. Then, the outer surface 5 of the cannula 1 was coated by spraying with antihemorrhagic substance—potassium aluminum sulfate dodecahydrate, thus leading to formation of an active layer 6. In vitro and in vivo studies have confirmed the role of this biopsy needle to accelerate the coagulation process.

EXAMPLE 6

The needle is made as described in Example 1, except that the outer surface 5 of the cannula 1 is coated with the active layer 6, as shown in FIG. 14 and FIG. 15. The active layer 6 contains a biologically active agent—fibrinogen, a protein which is involved in the coagulation process. Temporarily sealed cannula 1 was dipped ten times in an aqueous solution of fibrinogen (10 mg/ml), and dried temporarily. In vitro and in vivo studies have confirmed the role of this biopsy needle to accelerate the coagulation process and thus minimize the risk of bleeding.

EXAMPLE 7

The needle is made as described in Example 1, except that the active layer 6 is applied to the binder layer 7, which is applied on the outer surface 5 of the cannula 1 and the surface of the stylet 2, as shown in FIG. 16 and FIG. 17. The active layer 6 contains a biologically active antiseptic agent—zeolite, comprising of 2.5% silver ions and 14% zinc ions. The binder layer 7 is made of poly(vinyl alcohol). The binder layer 7 was obtained by biopsy needle immersion in acetone solution and drying. Then temporarily sealed cannula 1 was immersed in an aqueous solution of 0.5 mM/L of poly(vinyl alcohol) (molecular weight about 49 000 g·mol-1). Then, the binder layer 7 was coated by spraying with zeolit. The needle was dried in 50° C. for 1 hour to obtain the active layer 6 fixation.

EXAMPLE 8

The needle is made as described in Example 1, except that the outer surface 5 of the cannula 1 is coated with active layer 6 as shown in FIGS. 18-20. The surface of the active layer 6 is covered with a protective layer 8 to achieve stable release of the biologically active agent during whole prostate biopsy procedure. The protective layer 8 is made of poly(glycolic acid). The surface of the active layer 6 was coated by spraying with poly(glycolic acid) which forms a net-like protective layer 8. This layer delays the release of the biologically active agent from the active layer 6. The active layer 6 was obtained by mixing in a centrifuge (5 min, 30 rpm) antibiotic—levofloxacin with β-cyclodextrin in molal ratio 1:1. Further procedure was as described in Example 1, except that in the solution was immersed the temporarily sealed cannula.

EXAMPLE 9

The needle is made as described in Example 1, except that the outer surface 5 of the cannula 1 and stylet 2 surface have an extended form with porous pits, as shown in FIGS. 21-23. Pores 9a were obtained by micro laser engraving with a diameter of 0.1 mm and a depth of 0.05 mm. The active layer 6 is applied on an extended porous form 9a of the outer surface 5 of the cannula 1 and on an extended porous surface 9a of the stylet 2. The outer surface 5 of the cannula 1 and stylet surface 2 were coated with a mixture of β-cyclodextrin with ciprofloxacin in the molal ratio 1:1. Further procedure was as described in Example 1, except that in the solution was immersed the temporarily sealed cannula.

EXAMPLE 10

The needle is made as described in Example 1, except that the outer surface 5 of the cannula 1 and surface of stylet 2 have an extended form with grooved pits. The active layer 6 containing a complex of β-cyclodextrin with an antibiotic—ciprofloxacin was formed on extended grooved form 9b of the outer surface 5 of the cannula 1 and on the extended grooved form 9b of stylet 2, as shown in FIG. 24-26. Grooves 9b were formed parallel to the axis of the cannula 1 and stylet 2 to accumulate the antibiotic complex what allow an increase dose of active compound of the layer. The dimensions of the grooves 9b were 0.05 mm×0.05 mm×100 mm. Grooves 9b were obtained by micro laser engraving from the tip of the cannula 1 and stylet 2. The active layer 6 is applied on an extended grooved form 9b of the outer surface 5 of the cannula 1 and on an extended grooved surface 9b of stylet 2. The outer surface 5 of the cannula 1 and stylet surface 2 were coated with a mixture of β-cyclodextrin with ciprofloxacin in the molal ratio 1:1. Further procedure was as described in Example 1, except that in the solution was immersed the temporarily sealed cannula.

EXAMPLE 11

The needle is made as described in Example 1, except that the active layer 6 is applied on the outer surface 5 of the cannula 1, as shown in FIG. 27 and FIG. 28. The active layer 6 contains a biologically active antimicrobial agent—levofloxacin. The active layer 6 was obtained by mixing in a centrifuge (5 min, 30 rpm) antibiotic—levofloxacin with β-cyclodextrin in molal ratio 1:1. Further procedure was as described in Example 1, except that in the solution was immersed the temporarily sealed cannula. The surface of the active layer 6 is coated by spraying with the aqueous solution of 0.5 mM/L of poly(vinyl alcohol) (molecular weight about 49 000 g·mol-1) to form a protective layer 8 which was made to achieve stable release of the biologically active agent. The protective layer 8 had a thickness of 0.02 mm.

EXAMPLE 12

The biopsy needle is made as described in Example 1, except that the outer surface 5 of the cannula 1 is coated with two active layers 6, as shown in FIGS. 29-31. The first active layer 6 is applied to the binder layer 7 which is located on the outer surface 5 of the cannula 1. Binder layer 7 was obtained by dipping the cannula 1 in a solution of acetone and drying, and then dipping in an aqueous solution of 0.5 mM/L of poly(vinyl alcohol) (molecular weight of 49,000 g·mol-1). On such binder layer 7 the first active layer 6, obtained as described in Example 1, was applied, except that the cannula 1 was temporarily sealed. Then, the first active layer 6 was coated by spraying with poly(glycolic acid) which forms a net-like protective layer 8. This layer delays the release of the biologically active agent from the first active layer 6. The second active layer 6, was applied on the protective layer 8. The second active layer was obtained as in Example 1, except that the cannula 1 was temporarily sealed.

EXAMPLE 13

A steel biopsy needle with 200 mm length, comprises a pointed cannula 1, pointed stylet 2 slidably located in the cannula 1 and in the back the polypropylene holders for the biopsy gun—a cannula holder 3a and stylet holder 3b. The outer width of the cannula 1 is 1.52 mm, its height is 2.22 mm, and the stylet 2 diameter is 1.27 mm as shown in FIGS. 32-36. The cannula 1 has a circular cross-section and one axis of symmetry. The cannula 1 contains main channel with diameters of 1.32 mm (for the stylet) and a longitudinal pass-through-hole channel 10 of cannula 1. The additional channel 10 of circular shaped in cross section with the diameter of 0.5 mm, passes through 150 mm of cannula 1, beginning at its pointed end, protrudes over the outer surface 5 of the cannula 1 and then transfer into the steel connector 11. The connector 11 has a tube form, a length of 25 mm, an inner diameter of 0.5 mm and an external diameter 0.65 mm. The connector 11 of the channel 10 is connected to a flexible tube 12, made of poly(vinyl chloride), with an internal diameter of 0.5 mm and a length of 200 mm. The flexible tube 12 is connected with a 5 ml syringe 13. As shown in FIG. 39 by using the biopsy gun and a biopsy needle under transrectal ultrasound, prostate cores s were collected in a standard way. During the procedure, at each sequence of collecting biopsy samples 0.1 ml of an aqueous solution of levofloxacin (5 mg/ml) and 0.1 ml of lidocaine hydrochloride (20 mg/ml) were administered through the additional channel 10. In vitro and in vivo studies confirmed the antibacterial effect in the action area o of bioactive agents. The analgesic effect was confirmed in vivo.

EXAMPLE 14

A steel biopsy needle with 200 mm length, comprises a pointed cannula 1, pointed stylet 2 slidably located in the cannula 1 and in the back the polypropylene holders for the biopsy gun—a cannula holder 3a and stylet holder 3b. The outer width of the cannula 1 is 1.52 mm, its height is 2.22 mm, and the stylet 2 diameter is 1.27 mm as shown in FIGS. 34-38. Cannula 1 has a circular cross-section and one axis of symmetry. The cannula 1 contains main channel with diameters of 1.32 mm (for the stylet) and a longitudinal pass-through-hole channel 10 of cannula 1. The additional channel 10 of circular shaped in cross section with the diameter of 0.5 mm, passes through the entire length of the cannula 1, from its pointed end to the holder 3a. As shown in FIG. 39 by using the biopsy gun and a biopsy needle under transrectal ultrasound, prostate cores s were collected in a standard way. During the procedure, at each sequence of collecting biopsy samples 0.1 ml of an aqueous solution of levofloxacin (5 mg/ml) and 0.1 ml of lidocaine hydrochloride (20 mg/ml) were administered through the additional channel 10. In vitro and in vivo studies confirmed the antibacterial effect in the action area o of bioactive agents. The analgesic effect was confirmed in vivo.

The invention claimed is:

1. A prostate biopsy needle comprising:
   a front side;
   a back side;
   a cannula including an outer surface;
   a pointed stylet including a stylet surface, the pointed stylet configured to be mounted slidably in the cannula; and
   handles configured to engage a biopsy gun and located on the back side, the handles configured to be located on the back side of the needle,
   wherein a part of the outer surface of the cannula and/or a part of the stylet surface is coated with at least one active layer, the at least one active layer comprising an antibacterial substance, wherein the at least one active layer forms a biodegradable structure enabling controlled release of the antibacterial substance;
   wherein the coated part is an area ranged from 0.1 cm to 10 cm in length.

2. The needle according to claim 1, wherein the outer surface of the cannula and/or the stylet surface form an extended surface in a form of a grooved and/or rough and/or porous surface.

3. The needle according to claim 2, wherein the extended surface forms pits with depth ranged from 0.001 mm to 0.1 mm, preferably from 0.01 mm to 0.06 mm.

4. The needle according to claim 1, wherein the outer surface of the cannula is coated with the active layer, wherein a coated part is an area ranged from 4 cm to 8 cm, and/or the stylet surface is coated with the active layer, wherein a coated part is an area ranged from 4 cm to 8 cm.

5. The needle according to claim 1, in which the active layer is applied on a binder layer wherein the outer surface of the cannula and/or the stylet surface is coated with the binder layer.

6. The needle according to claim 1, in which the active layer contains a binder agent.

7. The needle according to claim 1, in which a surface of the active layer is coated with a protective layer enabling stable release of the biologically active agent, preferably in the form of polymer layer.

8. The needle according to claim 7, wherein the protective layer has a form of a fine mesh with the cells size from 1 μm to 500 μm, preferably 10 μm to 100 μm.

9. The needle according to claim 1, in which the antibacterial substance is an antibiotic and/or a chemotherapeutic agent and/or zinc ions and/or silver ions.

10. The needle according to claim 4, in which the coated part of the outer surface of the cannula extends from a tip of the cannula and/or the coated part of the stylet surface extends from a tip of the stylet.

* * * * *